United States Patent [19]

Weissman et al.

[11] Patent Number: 6,066,452
[45] Date of Patent: *May 23, 2000

[54] MULTIPLEX SELECTION TECHNIQUE FOR IDENTIFYING PROTEIN-BINDING SITES AND DNA-BINDING PROTEINS

[75] Inventors: Sherman M. Weissman; Girish N. Nallur, both of New Haven, Conn.; Prakash Kulkarni, Columbia, Md.

[73] Assignee: Yale University, New Haven, Conn.

[*] Notice: This patent is subject to a terminal disclaimer.

[21] Appl. No.: 08/906,691

[22] Filed: Aug. 6, 1997

Related U.S. Application Data

[63] Continuation-in-part of application No. 08/590,571, filed as application No. PCT/US97/01230, Jan. 24, 1997, Pat. No. 5,861,246.

[51] Int. Cl.[7] .............................. C12Q 1/68; C12P 19/34; C12N 15/63
[52] U.S. Cl. ................................ 435/6; 435/7.1; 435/7.8; 435/91.1; 435/91.2; 435/320.1; 435/440
[58] Field of Search .................................. 435/6, 7.1, 7.8, 435/91.1, 91.2, 172.3, 320.1, 440

[56] References Cited

U.S. PATENT DOCUMENTS 5,552,270  9/1996  Khrapko et al. ............................ 435/6

FOREIGN PATENT DOCUMENTS

WO 94/21825  9/1994  WIPO .
WO 94/27719  12/1994  WIPO .

OTHER PUBLICATIONS

Blackwell, "Selection of protein binding sites from random nucleic acid sequences", Meth. Enzymol. 254: 604–618, 1995.
Norby et al., "Determination of recognition–sequences for DNA–binding proteins by a polymerase chain reaction assisted binding site selection method (BSS) using nitrocellulose immobilized DNA binding proteins", Nucleic Acids Res. 20: 6317–6321, 1992.
Blackwell and Weintraub, "Differences and Similarities in DNA–Binding Preferences of MyoD and E2A Protein Complexes Revealed by Binding Site Selection," *Science 250:* 1104–1110, 1990.
Blackwell et al., "Sequence–Specific DNA Binding by the c–Myc Protein," *Science 250:* 1149–1151, 1990.
Chittenden et al., "The T/E1A–Binding Domain of the Retinoblastoma Product Can Interact Selectively with a Sequence–Specific DNA–Binding Protein," *Cell 65:* 1073–1082, 1991.

Ellington and Szostak, "In vitro selection of RNA molecules that bind specific ligands," *Nature 346:* 818–822, 1990.
Funk and Wright, "Cyclic amplification and selection of targets for multicomponent complexes: Myogenin interacts with factors recognizing binding sites for basic helix–loop–helix, nuclear factor 1, myocyte–specific enhancer–binding factor 2, and COMP1 factor," *Proc. Natl. Acad. Sci. USA 89:* 9484–9488, 1992.
Henrissat et al., "Cellulase families revealed by hydrophobic cluster analysis," *Gene 81:* 83–95, 1989.
Kinzler and Vogelstein, "Whole genome PCR: application to the identification of sequence bound by gene regulatory proteins," *Nucleic Acids Research 17*(10): 3645–3653, 1989.
Mavrothalassitis et al., "Laboratory Methods. Defining Target Sequences of DNA–Binding Proteins by Random Selection and PCR: Determination of the GCN4 Binding Sequence Repertoire," *DNA and Cell Biology 9*(10): 783–788, 1990.
Pierrou et al., "Selection of High–Affinity Binding Sites for Sequence–Specific, DNA Binding Proteins from Random Sequence Oligonucleotides," *Analytical Biochemistry 229:* 99–105, 1995.
Pollock and Treisman, "A sensitive method for the determination of protein–DNA binding specificities," *Nucleic Acids Research 18*(21): 6197–6204, 1990.
Rudert and Trucco, "DNA polymers of proteins binding sequences generated by PCR,"*Nucleic Acids Research 18*(21): 6460, 1990.
Thiesen and Bach, "Target Detection Assay (TDA): a versatile procedure to determine DNA binding sites as demonstrated on SP1 protein," *Nucleic Acids Research 18*(11): 3203–3209, 1990.
Tuerk and Gold, "Systematic Evolution of Ligands by Exponential Enrichment: RNA Ligands to Bacteriophage T4 DNA Polymerase," *Science 249:* 505–510, 1990.
Wright and Funk, "CASTing for multicomponent DNA–binding complexes," *Trends in Biochemical Sciences 18:* 77–80, 1993.

*Primary Examiner*—Scott D. Priebe
*Attorney, Agent, or Firm*—Foley & Lardner

[57] ABSTRACT

Methods for simultaneously selecting binding site sequences for multiple DNA-binding proteins are provided. A source of DNA-binding proteins is mixed with oligonucleotide duplexes containing a randomized internal sequence. Bound oligonucleotides are isolated, amplified and analyzed, such as by DNA sequence analysis. The oligonucleotide duplexes are also used to identify and isolate DNA-binding proteins.

30 Claims, 5 Drawing Sheets

SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
       (A) LENGTH:70 base pairs
       (B) TYPE:nucleic acid
       (C) STRANDEDNESS:single
       (D) TOPOLOGY:linear (ii) MOLECULE TYPE: DNA (xi) SEQUENCE DESCRIPTION: SEQ ID NO:1:

ATGCAAATNN NNNNNNNNNN NNNNAATCAG AANNNNNNNN NNNNNNNNNN                50

NNNNNNNNCT AGGGGAAGGG                                                 70

(2) INFORMATION FOR SEQ ID NO:2:

(i) SEQUENCE CHARACTERISTICS:
       (A) LENGTH:47 base pairs
       (B) TYPE:nucleic acid
       (C) STRANDEDNESS:single
       (D) TOPOLOGY:linear (ii) MOLECULE TYPE: DNA (xi) SEQUENCE DESCRIPTION: SEQ ID NO:2:

CGAGGTCGAC GGTATCGNNN NNNNNNNGGA TCCACTAGTT CTAGAGC                   47

(2) INFORMATION FOR SEQ ID NO:3:

(i) SEQUENCE CHARACTERISTICS:
       (A) LENGTH:17 base pairs
       (B) TYPE:nucleic acid
       (C) STRANDEDNESS:single
       (D) TOPOLOGY:linear (ii) MOLECULE TYPE: DNA (xi) SEQUENCE DESCRIPTION: SEQ ID NO:3:

CGAGGTCGAC GGTATCG                                                    17

(2) INFORMATION FOR SEQ ID NO:4:

(i) SEQUENCE CHARACTERISTICS:
       (A) LENGTH:19 base pairs
       (B) TYPE:nucleic acid
       (C) STRANDEDNESS:single
       (D) TOPOLOGY:linear (ii) MOLECULE TYPE: DNA (xi) SEQUENCE DESCRIPTION: SEQ ID NO:4:

GCTCTAGAAC TAGTGGATC                                                  19

(2) INFORMATION FOR SEQ ID NO:5:

(i) SEQUENCE CHARACTERISTICS:
       (A) LENGTH: 15 base pairs
       (B) TYPE: nucleic acid
       (C) STRANDEDNESS:single
       (D) TOPOLOGY: linear (ii) MOLECULE TYPE: DNA (xi) SEQUENCE DESCRIPTION: SEQ ID NO:5:

GAATAGAACT GGATC                                                                15

(2) INFORMATION FOR SEQ ID NO:6:

(i) SEQUENCE CHARACTERISTICS:
        (A) LENGTH:17 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:6:

ATCGGTAGGK GSGTCGA                                                              17

(2) INFORMATION FOR SEQ ID NO:7:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:7:

GGACCAATCG                                                                      10

(2) INFORMATION FOR SEQ ID NO:8:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:8:

TGGGTGGGGT                                                                      10

(2) INFORMATION FOR SEQ ID NO:9:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:9:

ACCTGATATG                                                                      10

(2) INFORMATION FOR SEQ ID NO:10:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:10:

GTGACTCCCG                                                                      10

(2) INFORMATION FOR SEQ ID NO:11:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:11:

GCCAAGGTCG                                        10

(2) INFORMATION FOR SEQ ID NO:12:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:12:

CCCATCCATG                                        10

(2) INFORMATION FOR SEQ ID NO:13:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:13:

GTAGCCATGT                                        10

(2) INFORMATION FOR SEQ ID NO:14:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:14:

ATGGTAGCGT                                        10

(2) INFORMATION FOR SEQ ID NO:15:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:15:

TCGCAATGGG                                        10

(2) INFORMATION FOR SEQ ID NO:16:

```
    (i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:16:

GGTAATAGGN                                                                      10

(2) INFORMATION FOR SEQ ID NO:17:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:17:

CTGGATTATG                                                                      10

(2) INFORMATION FOR SEQ ID NO:18:

(i) SEQUENCE CHARACTERISTICS:
        (A) LENGTH: 10 base pairs
        (B) TYPE:nucleic acid
        (C) STRANDEDNESS: single
        (D) TOPOLOGY:linear (ii) MOLECULE TYPE: DNA (xi) SEQUENCE DESCRIPTION: SEQ ID NO:18:

GTGGGGGGTT                                                                      10

(2) INFORMATION FOR SEQ ID NO:19:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:19:

GTGGGAGGGT                                                                      10

(2) INFORMATION FOR SEQ ID NO:20:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:20:

CATGGCGGAC                                                                      10

(2) INFORMATION FOR SEQ ID NO:21:

(i) SEQUENCE CHARACTERISTICS:
        (A) LENGTH:10 base pairs
        (B) TYPE:nucleic acid
        (C) STRANDEDNESS:single
```

(D) TOPOLOGY:linear (ii) MOLECULE TYPE: DNA (xi) SEQUENCE DESCRIPTION: SEQ ID NO:21:

GTCTAGGGAG                                                              10

(2) INFORMATION FOR SEQ ID NO:22:

(i) SEQUENCE CHARACTERISTICS:
            (A) LENGTH:10 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:22:

GGGGGGCTAT                                                              10

(2) INFORMATION FOR SEQ ID NO:23:

(i) SEQUENCE CHARACTERISTICS:
            (A) LENGTH:10 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:23:

GATTTGGACT                                                              10

(2) INFORMATION FOR SEQ ID NO:24:

(i) SEQUENCE CHARACTERISTICS:
            (A) LENGTH:11 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:24:

TAGGDGBAGG G                                                            11

(2) INFORMATION FOR SEQ ID NO:25:

(i) SEQUENCE CHARACTERISTICS:
            (A) LENGTH:16 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:25:

GGGGATGGGC GGATCC                                                       16

(2) INFORMATION FOR SEQ ID NO:26:

(i) SEQUENCE CHARACTERISTICS:
            (A) LENGTH: 16 base pairs
            (B) TYPE:nucleic acid
            (C) STRANDEDNESS:single
            (D) TOPOLOGY: linear (ii) MOLECULE TYPE: DNA (xi) SEQUENCE DESCRIPTION: SEQ ID NO:26:

TAGTGTGGGT GGATCC                                                              16

(2) INFORMATION FOR SEQ ID NO:27:

(i) SEQUENCE CHARACTERISTICS:
            (A) LENGTH:16 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:27:

ATTTATGGGG GGATCC                                                              16

(2) INFORMATION FOR SEQ ID NO:28:

(i) SEQUENCE CHARACTERISTICS:
            (A) LENGTH:16 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:28:

GTAGGTGGGC GGATCC                                                              16

(2) INFORMATION FOR SEQ ID NO:29:

(i) SEQUENCE CHARACTERISTICS:
            (A) LENGTH:17 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:29:

CGGAAGTGGC CGATACC                                                             17

(2) INFORMATION FOR SEQ ID NO:30:

(i) SEQUENCE CHARACTERISTICS:
            (A) LENGTH:16 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:30:

GACACGTGAT GGATCC                                                              16

(2) INFORMATION FOR SEQ ID NO:31:

(i) SEQUENCE CHARACTERISTICS:
            (A) LENGTH:10 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:31:

TATGGGGAA                                                                      10

(2) INFORMATION FOR SEQ ID NO:32:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:32:

GTGGGTGGGC     10

(2) INFORMATION FOR SEQ ID NO:33:

(i) SEQUENCE CHARACTERISTICS:
        (A) LENGTH:16 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:33:

GATTATGGGT GGATCC     16

(2) INFORMATION FOR SEQ ID NO:34:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:34:

GGTTGGGGGC     10

(2) INFORMATION FOR SEQ ID NO:35:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:35:

GTGGGCGGGG     10

(2) INFORMATION FOR SEQ ID NO:36:

(i) SEQUENCE CHARACTERISTICS:
        (A) LENGTH:10 base pairs
        (B) TYPE:nucleic acid
        (C) STRANDEDNESS:single
        (D) TOPOLOGY:linear (ii) MOLECULE TYPE: DNA (xi) SEQUENCE DESCRIPTION: SEQ ID NO:36:

GTGGGGGCTC     10

(2) INFORMATION FOR SEQ ID NO:37:

(i) SEQUENCE CHARACTERISTICS:

(A) LENGTH:16 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:37:

TGTCGTGGGT GGATCC                                                         16

(2) INFORMATION FOR SEQ ID NO:38:

(i) SEQUENCE CHARACTERISTICS:
            (A) LENGTH:10 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:38:

RTGGGBGGRY                                                                10

(2) INFORMATION FOR SEQ ID NO:39:

(i) SEQUENCE CHARACTERISTICS:
            (A) LENGTH:10 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:39:

AATTGTAAGC                                                                10

(2) INFORMATION FOR SEQ ID NO:40:

(i) SEQUENCE CHARACTERISTICS:
            (A) LENGTH:10 base pairs
            (B) TYPE:nucleic acid
            (C) STRANDEDNESS:single
            (D) TOPOLOGY:linear (ii) MOLECULE TYPE:DNA (xi) SEQUENCE DESCRIPTION: SEQ ID NO:40:

TTAGGTAAAT                                                                10

(2) INFORMATION FOR SEQ ID NO:41:

(i) SEQUENCE CHARACTERISTICS:
            (A) LENGTH:10 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:41:

CGCTGTAATA                                                                10

(2) INFORMATION FOR SEQ ID NO:42:

(i) SEQUENCE CHARACTERISTICS:
            (A) LENGTH:10 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:42:

CCGTAAAGGG                                                                          10

(2) INFORMATION FOR SEQ ID NO:43:

(i) SEQUENCE CHARACTERISTICS:
            (A) LENGTH:10 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:43:

GCCTATAACG                                                                          10

(2) INFORMATION FOR SEQ ID NO:44:

(i) SEQUENCE CHARACTERISTICS:
            (A) LENGTH:11 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:44:

GGGATAAACG C                                                                        11

(2) INFORMATION FOR SEQ ID NO:45:

(i) SEQUENCE CHARACTERISTICS:
            (A) LENGTH:10 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:45:

CATCATAACC                                                                          10

(2) INFORMATION FOR SEQ ID NO:46:

(i) SEQUENCE CHARACTERISTICS:
            (A) LENGTH:10 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:46:

AACCGGAAGT                                                                          10

(2) INFORMATION FOR SEQ ID NO:47:

(i) SEQUENCE CHARACTERISTICS:
            (A) LENGTH:12 base pairs
            (B) TYPE:nucleic acid
            (C) STRANDEDNESS:single
            (D) TOPOLOGY:linear (ii) MOLECULE TYPE: DNA (xi) SEQUENCE DESCRIPTION: SEQ ID NO:47:

```
CGTACCGGAA GG                                                                    12

(2) INFORMATION FOR SEQ ID NO:48:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:48:

CGATGGTAGA GGTGTGTGCG AATTCAGNNN NNNNNNNCGG AATTCACGTC GATCTTAGAA     60

CTGA                                                                 64

(2) INFORMATION FOR SEQ ID NO:49:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:49:

CGATGGTAGA GGTGTGTGC                                                 19

(2) INFORMATION FOR SEQ ID NO:50:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:50:

TCAGTTCTAA GATCGACGT                                                 19
```

MULTIPLEX SELECTION TECHNIQUE FOR IDENTIFYING PROTEIN-BINDING SITES AND DNA-BINDING PROTEINS

CROSS-REFERENCES TO RELATED APPLICATIONS

This application is a continuation-in-part of U.S. patent application Ser. No. 08/590,571, filed Jan. 24, 1996, now U.S. Pat. No. 5,861,246, and PCT/US 97/01230, filed Jan. 24, 1997, now pending.

STATEMENT OF GOVERNMENT INTEREST

This invention was made in part with funds provided by the United States Government. Accordingly, the United States Government may have certain rights to this invention.

TECHNICAL FIELD

The present invention relates generally to methods of identifying binding sites for DNA-binding proteins and methods of identifying DNA-binding proteins.

BACKGROUND OF THE INVENTION

The control of gene transcription in eukaryotes is largely controlled by myriad DNA-binding factors. Generally, such factors are required for initiation of transcription. Moreover, the presence of these factors may cause the activation of other transcription factors that control downstream processes and result in long term changes in gene expression. Thus, cellular differentiation and proliferation can be regarded as an integrated process involving the concerted and sequential action of transcription factors that determine the specific biology of the cell type.

Abnormal patterns of gene expression are the hallmark of several disorders and diseases. Such abnormal patterns may be the result of inappropriate expression, overexpression, or deficient expression of one or more genes. Deleterious consequences can flow from abnormal patterns. For example, overexpression of a growth factor can lead to a tumorigenic condition or a hyperproliferative disorder. In recognition of the importance of these processes, efforts to control gene expression is a major thrust of the biotechnology industry. Largely, these efforts focus on supplying extracellular signals that indirectly affect gene transcription or control post-transcriptional events. Where transcription factors that control particular genes have been identified, compounds are sought that directly affect transcription. However, this highly desirable approach to controlling gene expression has been hampered by the small number of transcription factors discovered.

A typical cell in humans expresses at least 10,000 genes. As many as 20% of these genes are believed to encode transcription factors. Each cell type could, therefore, express 2000 or more different transcription factors. However, only 10 to 20% of these factors have been identified. As well, only a fraction of the protein-binding sites have been identified. Several approaches for the selection of binding sites of individual DNA-binding proteins have been described (Irvine et al., *J. Mol. Biol.* 222:739, 1991; Blackwell and Weintraub, *Science* 250:1104, 1990; and Thieson and Bach, *Nucleic Acids Res.* 18:3203, 1990). These methods use single target macromolecules or nucleic acids for selection of totally or partially randomized oligonucleotide duplexes. The consensus DNA-binding sites for several proteins have been determined using these approaches (Wright and Funk, *Trends Biochem. Sci.* 18:77, 1993). Another approach, called CASTing (Funk et al., *Proc. Natl. Acad Sci. USA* 89:9484, 1992), has been used to identify transcription factors that bind adjacent to, and cooperate with, a specific factor for which an antibody is available. All these techniques suffer major disadvantages: the identification of binding sites or transcription factors is time-consuming, tedious, often requires large amounts of biological material, or depends upon the availability of mutants. In general, these techniques yield only one new factor or one new binding site at a time.

The present invention provides a direct approach for the simultaneous isolation and characterization of binding sites recognized by a large cross-section of the transcription factors present in any cell type. These binding sites subsequently facilitate isolation of transcription factors as well as providing other related advantages.

SUMMARY OF THE INVENTION

In a preferred aspect, the present invention provides a method for isolating DNA-binding proteins, comprising: (a) mixing a set of oligonucleotide duplexes comprising 5' and 3' sequences that will hybridize to primers for amplification and an internal sequence of random nucleotides, an inhibitor of non-sequence specific binding of DNA-binding proteins to the oligonucleotide duplexes and a sample containing a mixture of DNA-binding proteins under conditions in which the concentration of oligonucleotide duplexes is at or below the average Kd value for specific binding between the oligonucleotide duplexes and the DNA-binding proteins; (b) separating unbound oligonucleotide duplexes from oligonucleotide duplexes complexed with the DNA-binding proteins on the basis of differences in physical or biochemical properties; (c) recovering the DNA-binding proteins from the complexes.

In preferred embodiments, subsequent to step (b): the complexed duplexes are amplified, mixed with the sample containing DNA-binding proteins; and separated on the basis of differences in physical or biochemical properties; wherein the amplifying, mixing, and separating steps are performed one or more times. In especially preferred embodiments, the steps are performed three times. In other preferred embodiments, the sample is a nuclear extract, a cellular extract or intact nuclei.

In yet other preferred embodiments, the internal sequence is a random sequence, is from about 6 to about 25 base pairs or is from about 8 to about 12 base pairs. In still other preferred embodiments, the 5' and 3' sequences are from about 10 to about 30 bp. A preferred method of separation is based on differences in mobility, such as polyacrylamide gel electrophoresis or size-exclusion chromatography, or is based of differences in filter-binding properties.

In another aspect, the invention provides a method for identifying DNA-binding proteins in an expression library, comprising: (a) screening a library of clones with the protein-binding sites obtained according to the steps outlined above, wherein the protein-binding sites include a detectable marker; and the detecting protein-binding sites bound to clones are detected. Preferably, the clones are isolated.

In another related aspect, the invention provides a method for simultaneously determining nucleotide recognition sequences for DNA-binding proteins, comprising the steps outlined above, further comprising analyzing the amplified duplexes to determine nucleotide recognition sequences for the DNA-binding proteins. In preferred embodiments, the analyzing step comprises ligating the amplified duplexes to a vector to generate clones; and determining the DNA sequences of the cloned duplexes. In other preferred embodiments, the analyzing step comprises denaturing the amplified duplexes; hybridizing the denatured duplexes to an array of single-stranded oligonucleotides having different sequences; and detecting oligonucleotides hybridized with denatured duplexes.

In yet another aspect, methods are provided for simultaneously isolating nucleotide recognition sequences for DNA-binding proteins, comprising the steps outlined above. In preferred embodiments, the method further comprises, mixing the amplified duplexes with the sample containing DNA-binding proteins; separating unbound amplified duplexes from amplified duplexes complexed with the DNA-binding proteins on the basis of differences in molecular weight; and amplifying the complexed duplexes from step (c)(2) to form amplified duplexes; wherein steps (c)(1) through (c)(3) are performed one or more times. In especially preferred embodiments, the steps are performed three times, the 5' and 3' sequences each have a restriction site.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

DETAILED DESCRIPTION OF THE INVENTION

Figure 1:
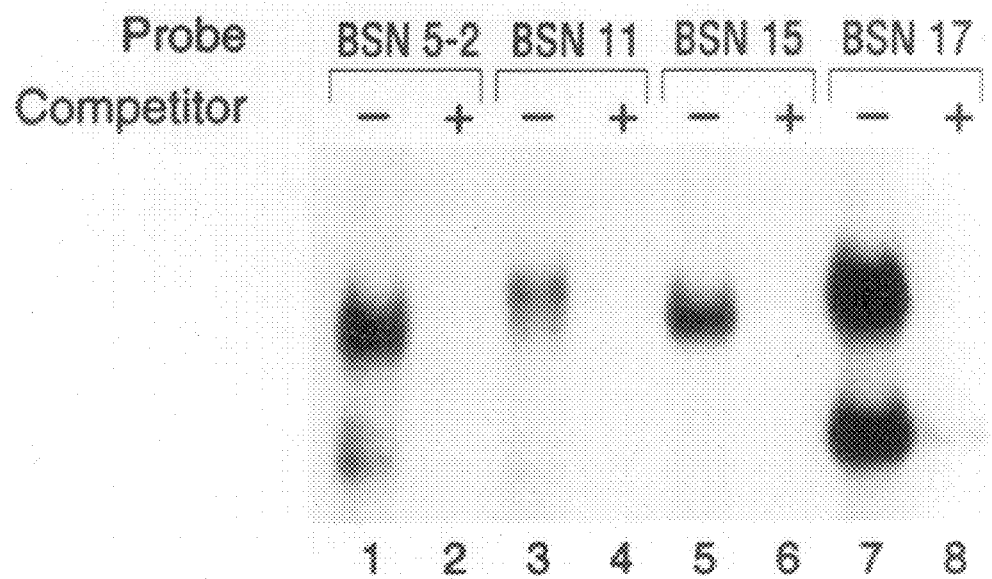
FIG. 1 is an autoradiogram of a gel shift analysis of the oligonucleotide duplexes presented in Table 1 after complexing with HA-TP2 nuclear extract. Only those duplexes that exhibit a gel-shift are shown. Lanes marked with a "+" represent gel-shift assays performed in the presence of 50-fold excess of unlabeled oligonucleotide duplex.

Prior to setting forth the invention, it will be helpful to an understanding thereof to set forth definitions of certain terms used herein.

Deoxynucleotides, or nucleotides, are referred to according to standard abbreviations: "A", deoxyadenylate; "C", deoxycytidylate; "G", deoxyguanylate; "T", deoxythymidylate; "M", A or C; "R", A or G; "W", A or T; "S", C or G; "Y", C or T; "K", G or T; "V"A, C, or G; "H", A, C or T; "D", A, G, or T; "B", C, G-. or T; and "N", A, C, T, or G.

A. Multiple Selection Technique

As noted above, the present invention provides methods for simultaneously determining protein-binding sites for DNA-binding proteins. Briefly, in these methods, a set of oligonucleotide duplexes having an internal sequence containing a potential nucleotide recognition sequence (i.e., protein-binding site) and 5' and 3' sequences that anneal to amplification primers is mixed in the presence of a non-specific inhibitor with a sample that contains DNA-binding proteins, such as a cell extract, a nuclear extract, whole nuclei or expression library. DNA-binding proteins bind to their respective recognition sequences to form DNA-protein complexes. Bound oligonucleotide duplexes are then separated from unbound (i.e., free) duplexes generally on the basis of physical, chemical, or biochemical properties, such as differing mobility or molecular weight. The oligonucleotides in the bound duplexes are amplified and may be subsequently analyzed or isolated. Prior to analysis, the method may be repeated: amplified duplexes are mixed with a sample containing DNA-binding proteins, the bound duplexes are isolated, and the oligonucleotides in the bound duplexes are amplified. These steps can be repeated as many times as necessary to yield desired levels of enrichment and selection of binding sites.

Thus, starting with a complex mixture of oligonucleotide duplex targets in a small number of selection cycles, one can obtain a mixture that is predominantly made up of specific oligonucleotide duplexes containing optimal protein-binding sites. By starting with two complex mixtures (i.e., oligonucleotide duplexes and DNA-binding proteins), a high fraction of specifically bound duplexes is obtained while minimizing amounts of bound duplexes having lower affinity. As multiple, independent DNA-protein interactions occur simultaneously in these methods, the method is referred to as the Multiplex Selection Technique, or MuST™.

B. Design of Oligonucleotide Duplexes Containing Protein-binding Sites

As described above, oligonucleotide duplexes have a tripartite structure: an internal sequence containing a potential protein-binding site and 5' and 3' sequences capable of annealing to primers for amplification.

Typically, the internal sequence comprises a randomized base sequence. The internal sequence has a minimum length of 4, 5, or 6 base pairs, which is approximately the length of sequence bound by a DNA-binding protein. Although there is no theoretical upper limit on the length of the internal sequence, typically the length will not be longer than 15, 20, 25, 30, or 35 bp, and preferably the length is 8, 9, 10, 11, or 12 base pairs. By using one of these preferred lengths, generally only one binding site is present per oligonucleotide duplex, decreasing the chance of selecting oligonucleotide duplexes that contain separate binding sites for two different proteins. This avoids confusion about interaction between proteins separately bound to DNA, but increases the likelihood of obtaining a single optimal site for each protein. In turn, this simplifies the analysis of data and cataloging of DNA-binding sites. At times, it may be preferable to use an internal sequence that has a random sequence of a length sufficient to bind a DNA-binding protein adjacent to a sequence that has a defined sequence that binds a known DNA-binding protein. In such case, a source of the known DNA-binding protein is provided, as part of or in addition to, the sample of DNA-binding proteins.

Furthermore, the internal sequence is randomized, that is each position has an equal probability of having any of the four deoxynucleotides (A, C, G, or T). Alternatively, the internal sequence could be partially randomized, such as randomizing a subset of the positions or fixing the probability of the four nucleotides at other than a 1:1:1:1 ratio. For example, some DNA-binding proteins bind to G–C or A–T rich regions. Duplexes with higher percentages of G+C or A+T can be synthesized. As well, other bases, such as inosine, uracil, 5-methylcytosine, 8-azaguanine, 2,6-diaminopurine, 5bromouracil, and other derivatives may be incorporated in their nucleotide form into the oligonucleotide duplexes.

The 5' and 3' sequences serve to allow annealing of specific primers for amplification of oligonucleotide duplexes. As such, the length of these flanking sequences should be appropriate for amplification. Typically, the length is 17 to 25 bp, although a shorter or longer length may be used. The 5' and 3' sequences are preferably different or distinct enough to avoid annealing to each other at times when the oligonucleotide is present as a single strand. In addition, the terminal 3' base sequences of the amplification primers should not be complementary, so as to avoid the formation of primer-dimers during amplification. Moreover, the base content is preferably average G+C (e.g., 40–50%). To facilitate cloning of the recovered, amplified oligonucleotide duplexes, restriction sites are optionally incorporated into the flanking sequences. The restriction sites can be identical, for non-directional cloning, or different, for directional cloning.

Oligonucleotides are generally synthesized as single strands by standard chemistry techniques, including automated synthesis. Many methods have been described for synthesizing oligonucleotides containing a randomized base. For example, a randomized position can be achieved by in-line mixing or using pre-mixed phophoramidite precursors during an automated procedure. (see, Ausbel et al., *Current Protocols in Molecular Biology*, Greene Publishing, N.Y., 1995) Oligonucleotides are subsequently de-protected and may be purified by precipitation with ethanol, chromatographed using a sizing or reversed-phase column, denaturing polyacrylamide gel electrophoresis, high-pressure liquid chromatography (HPLC), or other suitable method. In addition, within certain preferred embodiments, a functional group, such as biotin, is incorporated in the oligonucleotide duplex, preferably at the 5' and 3' terminal nucleotide. A biotinylated oligonucleotide may be synthesized using pre-coupled nucleotides. Alternatively, biotin may be conjugated to the oligonucleotide using standard chemical reactions. Because the group facilitates removal of the 5' and 3' sequences, the group should be reactive with an antibody or other molecule that will capture the sequences. Other functional groups, such as fluorescent dyes, digoxigenin, and the like, may be incorporated in the duplexes, and particularly at the 5' or 3' end. In other embodiments, functional groups are incorporated into the oligonucleotide internal sequence.

Duplexes are formed from single-stranded oligonucleotides either by annealing complementary single-stranded oligonucleotides that are chemically synthesized or by enzymatic synthesis. For chemical synthesis, the complementary strand is synthesized, deprotected and optionally purified as described above. The two oligonucleotide strands are mixed together in a buffered salt solution (e.g., 1 M NaCl, 100 mM Tris-HCl pH 8.0, 10 mM EDTA) or in a buffered solution containing $Mg^{2+}$ (e.g., 10 mM $MgCl_2$) and annealed by heating to high temperature and slow cooling to room temperature. For enzymatic synthesis, a primer complementary to the 3' end of the single-stranded oligonucleotides is annealed to the oligonucleotides. Buffer, dNTPs, and a DNA polymerase, such as the large fragment of *E. coli* DNA polymerase I (Klenow fragment), T4 DNA polymerase, or Taq DNA polymerase, is added and the reaction mixture is incubated at a temperature appropriate for the polymerase. Following synthesis, the enzyme is inactivated by heat or phenol-chloroform extraction, and the oligonucleotide duplexes may be purified as described herein. Enzymatic synthesis of the complementary strand assures that the internal sequence contains perfectly matched base pairs.

C. Preparation of a Sample Containing DNA-binding Proteins

As noted above, oligonucleotide duplexes are mixed with a sample that contains DNA-binding proteins. The sample or source can be a cell extract, nuclear extract, whole, purified nuclei or proteins from an expression library. When the internal sequence contains a known binding site, a source of purified binding protein may be added. Any cell or tissue can be used within the context of this invention for preparation of a source containing DNA-binding proteins. Thus, cells may be obtained from tissue culture or from tissue isolated from an organism, such as humans, animals, or plants.

A variety of methods can be used to prepare nuclear extracts (see, Ausebel et al., supra). Many of these methods share a common strategy of lysing cells without disrupting the nuclei, isolating the nuclei, and then disrupting the nuclear membrane. Briefly, within preferred embodiments, to prepare nuclear extracts from cell suspensions, cells are incubated on ice in a hypotonic (low-salt) buffer, which swells the cells. The buffer preferably contains protease inhibitors, such as PMSF, aprotinin, leupeptin, and trypsin inhibitor, and chelators of divalent cation, such as EDTA. The cell membrane is lysed by the addition of a non-ionic detergent (e.g., NP-40) or by homogenization with a Dounce homogenizer. Intact nuclei are collected by centrifugation. When tissue is used as a sample source, it is processed by standard techniques to isolate nuclei. Briefly, the tissues are first homogenized in a sucrose-containing buffer to yield sub-cellular components. Alternatively, the tissue can be teased into a single cell suspension and processed as for tissue culture cells. The intact nuclei are harvested by low speed centrifugation. Nuclei isolated from cells or tissue are lysed by the addition of a high-salt buffer, which extracts nuclear proteins, except for histones. It may be necessary to vortex, homogenize or otherwise mechanically disrupt the nuclear membrane for maximal extraction. The extract is clarified by centrifugation and subsequently desalted by dialysis or other equivalent method. Nuclear extracts may be used without further manipulation or may be further purified. Methods for further purification generally rely upon ionic interactions and include heparin-agarose (HA) chromatography (resulting in an HA-nuclear extract), Bio-Rex 70 ionic exchange chromatography, salmon sperm DNA chromatography, and the like. Proteins that bind to one of these substrates are eluted and used in the subsequent steps described herein. The extracts may be used immediately or stored at −70° C.

Alternatively, intact nuclei are isolated (Hagenbüchle and Wellauer, *Nucl. Acids Res.* 20:3555, 1992) and used within the present invention. Briefly, cells or tissue are resuspended in cold buffer (e.g., 60 mM KCl, 15 mM NaCl, spermine, spermidine, HEPES, DTT, and protease inhibitors) containing 0.3 M sucrose. Non-ionic detergent such as NP-40 is added and cells are disrupted mechanically by homogenizing in a Dounce homogenizer. The homogenate is layered on top of a cushion of the above buffer containing 0.9 M sucrose and centrifuged. The nuclear pellet is resuspended by homogenization in the above buffer containing 0.3 M sucrose and 0.2% NP-40 and centrifuged again through a 0.9 M sucrose cushion. The nuclear pellet is resuspended in buffer (e.g., containing 75 mM NaCl, EDTA, Tris, DTT, PMSF, and glycerol), centrifuged, and finally resuspended in buffer. This nuclear suspension is used directly in subsequent steps or stored at −70° C. prior to use.

D. DNA-protein Complex Formation

As noted above, a sample containing DNA-binding proteins, oligonucleotide duplexes, and non-specific inhibitor are mixed together to form a binding reaction. The binding reactions are typically incubated on ice for a short time, approximately 10 minutes. In the reactions exemplified herein, an extract containing approximately 1.4 μg of protein is mixed with 1–2 ng of labeled oligonucleotide duplexes and 1 μg of non-specific inhibitor in an appropriate buffer.

Several parameters are considered in setting up the reactions. The enrichment of specific binding sites is determined by various criteria, including, the dissociation constant ($K_d$) of the DNA-binding protein and protein-binding site, the relative ratios of DNA-binding protein to protein-binding site, and the length of DNA sequence recognized by the protein. Selection of the highest affinity binding sites is largely dependent upon the use of optimum conditions that yield the highest ratio of specific to non-specific binding sites selected for each interaction. In general, the selection of preferred binding sites is favored when the concentration of specific binding sites is at or below the dissociation constant for the complex between the DNA-binding protein and the protein-binding site. In a complex mixture, the concentration is preferably at or below an average dissociation constant for DNA-binding proteins and their binding sites. In such a case, there is good discrimination between optimum and suboptimum binding sites, even in the presence of an excess of the DNA-binding protein.

The concentration of a 10-mer binding site in the experiments reported herein is $5 \times 10^{-15}$ M, for a 6-mer binding site it is $5 \times 10^{-12}$ M. The concentration of a DNA-binding protein is estimated to be $3.5 \times 10^{-10}$ M (assuming a mass of 40 kD and an abundance level of 1:10,000 with respect to the total mass of protein). Under these conditions, the concentrations of individual binding sites, including small binding sites, and a single DNA-binding protein is well below the average $K_d$ value (assumed to be $10^{-8}$) for DNA-binding proteins and their binding sites. Therefore, in the present invention, the binding is not driven to saturation by either the binding site or the protein, resulting in discrimination of optimal and sub-optimal sites. At the same time, because multiple DNA-binding proteins are present in the mixture, the total amount of oligonucleotide duplex bound specifically by some proteins is relatively high compared to the background of non-specifically retained oligonucleotide duplex. The ratios of binding sites selected by two proteins is determined by the mathematical equation:

$$\left[\left(\frac{P_1}{P_2}\right)\left(\frac{K_1}{K_2}\right)\right]^n$$

wherein $P_1$ and $P_2$, $K_1$, and $K_2$ are the concentrations (P) and binding constants (K) of the two proteins, and "n" is the number of cycles of selection. In view of the large number of binding proteins in a sample, the total ratio of specific to non-specifically retained oligonucleotide duplexes will be relatively high at each cycle, and only a limited number of cycles of selection (e.g., 1 or more) are needed to obtain a set of duplexes in which most represent specific binding sites.

Non-specific interactions that might result from the binding of any single- or double-stranded oligonucleotides, ends of duplex molecules, or hairpin loops of the duplexes by proteins present in the nuclear extracts, can be diminished by including a non-specific inhibitor in the binding reaction. An exemplary non-specific inhibitor is poly(dI-dC), although any other homopolymer, RNA (e.g., yeast RNA) DNA from a heterologous organism (e.g., salmon sperm or *E. coli* DNA), and the like may be used. As well, non-specific interactions due to binding of proteins to mis-matched base pairs ("bubbles") present in the oligonucleotide duplexes may be minimized by preparing the second strand of the duplexes by enzymatic synthesis.

Some proteins may bind within or partially within the 5' and 3' sequences of the oligonucleotide duplexes (see Table 2 below). Such binding can be distinguished from binding within the internal portion of the oligonucleotide duplex. If binding is dependent on the flanking sequences, no binding will be detected if the duplex has different 5' and 3' sequences. Thus, changing the 5' and 3' sequences in subsequent cycles of selection will lessen the likelihood of such binding.

E. Isolation of Oligonucleotide Duplexes Complexed with DNA-binding Proteins

As described above, complexes of oligonucleotide duplexes that have a bound protein are separated from unbound oligonucleotide duplexes. Generally, separation depends upon physical, chemical, or biochemical differences. A convenient, simple, rapid, and sensitive method for separating DNA-protein complexes is gel electrophoresis. In a gel, an oligonucleotide duplex with a bound protein has retarded mobility relative to the unbound duplex (gel-shift). Alternatively, other methods can be used that rely on differing properties of DNA-protein complexes and free DNA, such as binding of the complexes to filters (e.g., nitrocellulose filters), HPLC, other sizing chromatography methods, capillary electrophoresis (Xian et al, *Proc. Natl. Acad. Sci. USA* 93:86, 1996) or conjugating either the oligonucleotide duplexes or DNA-binding proteins to a solid substrate (e.g., plastic, silica, glass).

Briefly, in the gel-shift method, the duplexes are labeled, usually with a radiolabel (e.g., $^{32}P$), biotin, digoxigenin, fluorescent dyes, or any other molecule that can be detected, mixed with the sample containing DNA-binding proteins and electrophoresed through the gel (see, Ausebel et al., supra). The gel is usually a low-percentage, low-ionic strength polyacrylamide-bisacrylamide gel. For example, a 4% gel with an acrylamide:bisacrylamide ratio of 19:1 is suitable. However, other buffer systems and percentage gels may be used. For example, a Tris-glycine (high ionic strength) buffer can be used, although if the ionic strength is too high, some protein-DNA interactions may be disrupted. When radiolabeled duplexes are used, following electrophoresis, the gel is dried onto a solid substrate (e.g., Whatman 3MM paper) and autoradiographed. Bands corresponding to protein-DNA complexes are excised and eluted into buffer. The oligonucleotides are then amplified using primers corresponding to the 5' and 3' sequences of the oligonucleotides. As discussed above, additional cycles of binding, separating and amplifying may be performed.

Partitioning the DNA-protein complexes in the gel can facilitate analysis by decreasing the complexity. Thus, as shown in the examples, different levels of DNA-binding proteins between two states of activation of a cell line become more pronounced.

F. Characterization and Use of Protein-binding Sites

Following the selection steps as discussed above, the oligonucleotide duplexes containing protein-binding sites may be isolated, utilized, analyzed or characterized. Various methods of analysis are available and the choice depends in part on the information desired. Thus, the selected duplexes may be subjected to DNA sequence analysis, used to facilitate isolation of the corresponding DNA-binding protein(s), administered to cells or cell-free transcription systems to bind available corresponding DNA-binding protein and inhibit transcription, and the like.

DNA sequences of the binding sites may be readily determined. In general, oligonucleotide duplexes are cloned individually or as concatamers into an appropriately prepared vector. Many vectors have been developed for directly cloning amplified products (e.g., pBluescript vector, PCR-Script vector or pGEM-1 vectors). Alternatively, when restriction sites are incorporated into the 5' and 3' sequences, the amplified material is preferably digested and cloned into a similarly digested vector. For exemplary purposes, EcoRI restriction sites are incorporated into the oligonucleotide duplexes. After amplification, the amplified DNA is digested with EcoRI and ligated to an EcoRI cut (and preferably also treated with alkaline phosphatase) vector, such as pBluescript (Stratagene Cloning Systems, La Jolla, Calif.). As well, when restriction sites are used, multimers of binding sites can be cloned. To facilitate cloning of multimers, preferably biotin or another readily detected group is added to the ends of the duplex. After restriction digestion, the 5' and 3' flanking sequences are removed with streptavidin-coupled beads or other capture molecule coupled to a solid substrate. The free binding sites are then ligated at high concentration to favor concatamer formation. The multimerized binding sites are ligated into a vector and transformed into bacteria.

Recombinant clones containing protein binding sites may be isolated and the DNA sequences of the inserts determined. Many methods for preparing DNA for sequence analysis and sequence techniques are readily available (see, Ausebel et al., supra). For example, plasmid DNA is recovered from lysed bacteria or single-stranded phagemid DNA is recovered from phage particles. Enzymatic sequence reactions may be performed on either denatured, double-stranded templates or single-stranded templates. Furthermore, sequence reactions may incorporate radiolabeled nucleotides or fluorescent-labeled nucleotides. Automated methods for determining the sequence from a gel are commonly used. Databases of binding site sequences are thus generated. These sequences may be compared to databases of known binding site sequences (e.g., Transfac database) and categorized by consensus sequence, base composition, known factor binding, and the like.

Alternatively, amplification of the duplexes can be performed with fluorochrome-tagged or radiolabeled nucleotides. The duplexes are then melted and hybridized to arrays of short single-stranded oligonucleotides of known sequence immobilized to a "chip" under conditions that favor exact match hybridization. Areas with detectable tags or label are identified, thus obtaining the sequence of the selected binding site. (see, U.S. Pat. Nos. 5,474,796; 5,436, 327; 5,429,807; 5,412,087; 5,436,327; 5,510,271; 5,445, 934; EP Patent No. 0 373 203 B 1.)

The binding site sequences can also be used to identify the corresponding DNA-binding proteins in an expression library. As shown in the examples, oligonucleotide duplexes containing one or more binding sites are labeled and used to probe an expression cDNA library. The library is usually constructed in a lambda vector, such as λgt 11, or in a plasmid or phagemid vector (e.g., pCDNA2.1, pSE240; pBlueBac; pcDNA3.1). Plaques or colonies that express a protein that binds the labeled duplex are isolated (see also, Ausebel, supra). The insert may then be subjected to DNA sequence analysis and/or used to isolate a full-length cDNA clone.

Alternatively, oligonucleotide duplexes containing one or more binding sites are used to isolate sequence-specific DNA-binding proteins that may be sequenced by mass spectrometry (see, Patterson and Aebersold, *Electrophoresis* 16:1791, 1995; Hunt et al., *Proc. Natl. Acad. Sci. USA* 83:6233, 1986; Figeys et al., *Nature BioTechnology* 14:1579, 1996. Based on the amino acid sequence of the DNA-binding protein generated by mass-spectometry, degenerate oligonucleotide probes can be synthesized and used to screen a cDNA or genomic library to isolate the coding sequence.

The binding sites can also be used to quantitatively or qualitatively determine DNA-binding proteins present in cell populations. Briefly, oligonucleotide duplexes are printed onto a "chip" in an array. Proteins from nuclear extracts, cellular extracts or the like are contacted with the duplexes on the chip. Bound proteins are detected. The proteins can be labeled with a radioactive label, fluorescent label or the like to aid in detection. Other detection systems that can detect bound, unlabeled proteins may also be used. By detecting binding to a particular duplex sequence, the presence or quantity of protein in the extract is measured. Extracts can be prepared from different cell populations, such as activated and non-activated cells, tumor and normal cells, cells from different tissues and the like. Comparison of binding patterns will reveal differences in expression of binding proteins.

The binding site can be transfected into cells such that the available DNA-binding protein is bound to the introduced site, effectively inactivating the protein. For example, a particular transcription factor can be inhibited by introducing its binding site in high amounts, such as in a liposome complex containing the oligonucleotide duplex (Morishita, et al., *Proc. Natl. Acad. Sci. USA* 92:5855, 1995). By this method, gene expression can be modulated and proliferation or differentiation can be inhibited.

In addition, the binding site can be used to select antibody expressing phages. A crude nuclear extract or a complex of a long DNA probe with multiple binding proteins attached may be used to enrich phage expressing antibodies or portions of antibodies (Nissim et al., *EMBO J* 13:692, 1994; Smith, *Science* 228:1315, 1985; Parmley and Smith *Gene* 73:305, 1988; U.S. Pat. No. 5,223,409). The complexes may be immobilized, for example on a plastic surface, unbound phage washed off, and bound phage eluted.

With the availability of cDNA clones encoding sequence-specific DNA-binding proteins, anti-sense RNA molecules may be generated by in vitro transcription of the cDNA and introduced into cells to inhibit the function of a given DNA-binding protein. Anti-sense RNA could also be introduced by a cloning vector that directs the transcription of anti-sense RNA.

G. Identification and Isolation of DNA-binding Proteins

As noted above, the binding site sequences can be used in various ways to identify and isolate DNA-binding proteins. In one approach, isolated binding site sequences are labeled and used as probes on an expression library. An expression library is generally constructed in a bacteriophage vector (e.g., λ), in a plasmid vector (e.g., pCDA3.1; pBlueBac) or in a phagemid (e.g, pBluescript). The techniques for generating libraries are well-known (see e.g., Sambrook et al., Molecular Cloning: A Laboratory Approach, Cold Spring Harbor Press, 1989; Ausbel et al., Current Protocols in Molecular Biology, Greene Publishing Co., 1996). The libraries are transfected into an appropriate host cell, generally a bacteria, and propagated. Transformed cells are probed with a labeled binding-site sequence(s). The binding sites are isolated according to the methods described herein. The binding sites can be amplification products, which will contain one or more sequences, or clones of individual binding sites. In any case, the binding site sequences are labeled according to an acceptable method for the type of label. Thus, a radioactive label can be incorporated during amplification by way of free nucleotides or labeled primer, added by end-labeling using $T_4$ polynucleotide kinase, DNA polymerase I (if there is a 5' overhang) or other similar method. Other labels, such as biotin, can be incorporated into primers used for amplification or chemically conjugated. Many methods are available for labeling (see Sambrook et al., supra; Ausebel et al., supra). When a clone in the expression library is identified by binding to a binding site sequence, it may be purified and subjected to further analysis, such as DNA sequence determination. In addition, or alternatively, the clone insert can be used to identify a full-length insert in the same or different library. The full-length insert can be subjected to DNA sequence analysis, expressed, used as a hybridization probe on cells, isolated RNA, and the like. Antisense oligonucleotides can be used to inhibit expression of the protein in a cell.

DNA-binding proteins can alternatively be isolated from the complexes of oligonucleotide-protein complexes that are formed as described herein. Briefly, in this method, a set of oligonucleotide duplexes 3 having 5' and 3' sequences capable of annealing to primers for amplification and an internal sequence having a random sequence is mixed in the presence of a non-specific inhibitor with a sample containing DNA-binding proteins (e.g., nuclear extract). Duplexes bound with DNA-binding proteins are separated from unbound duplexes and unbound proteins. The bound proteins are then recovered from the complexes. The oligonucleotide duplexes can also be isolated after multiple rounds of selection (e.g., 2, 3, 4, 5, or 6 rounds). Such duplexes may be more restricted in the sequences of the internal sequence and as a consequence the binding proteins may comprise a smaller set of proteins.

The following examples are offered by way of illustration, and not by way of limitation.

EXAMPLES

Example 1

NUCLEAR EXTRACT PREPARATION

Jurkat cells, a human T cell line, are grown in RPMI 1640 medium containing 10% (v/v) fetal bovine serum. For some experiments, activated Jurkat cells are used. For activation, cells are serum-starved in RPMI 1640 medium for 24 hours and replenished with 10% fetal bovine serum at a density of $0.2 \times 10^6$ cells per ml and either 50 ng of PMA (phorbol 12-myristate 13-acetate) or 2 μg of PHA (phytohemagglutinin) alone or in combination are added per ml of cell culture for 4 hours.

Approximately $10^8$ cells are harvested at different time intervals by centrifugation at 700×g for 5 min in 50 ml conical tubes. Cells are resuspended in 10 ml TBS (Tris-buffered saline) and pelleted by centrifugation (1000×g for 10 min, at 4° C.). Cells are then suspended in 10 ml of cold Buffer A (10 mM HEPES pH 7.9, 10 mM KCl, 0.1 mM EDTA, 0.1 mM EGTA, 1 mM DTT, 0.5 mM PMSF, 2 μg/ml aprotinin, 1 μg/ml leupeptin, and 10 μg/ml trypsin inhibitor) by gentle trituration and incubated on ice for 15 min. Following incubation, 600 μl of 10% NP-40 are added. The cells are vortexed vigorously for 10 sec and centrifuged at 1500×g for 10 min at 4° C. The pellet is suspended in 1 ml of cold Buffer C (20 mM HEPES pH 7.9, 0.4 M NaCl, 1 mM EDTA, 1 mM EGTA, 1 mM DTT, 1 mM PMSF) and transferred to an Eppendorf tube. The tube is vigorously rocked for 15 min at 4° C., then centrifuged in an Eppendorf centrifuge for 10 min at 10,000 rpm at 4° C. Supernatant is then dialyzed in 2 L cold Buffer A at 4° C. to lower the salt concentration. Following dialysis, supernatant is clarified by centrifugation at 1500×g for 10 min at 4° C.

The crude nuclear extract may be further fractionated on a heparin-Sepharose column. The extract is passed over a column equilibrated in 0.1 M NaCl. Nuclear proteins are eluted in 0.4 M NaCl. The amount of protein in the extracts is measured by a colorimetric assay (Bradford assay) before and after applying the supernatant to the column. The crude extract or fractionated extract is snap-frozen in liquid $N_2$ or ethanol/dry ice in 20 μl aliquots and stored at −70° C.

Example 2

COMPLEX FORMATION BETWEEN NUCLEAR EXTRACT AND OLIGONUCLEOTIDE DUPLEXES

A typical binding reaction is carried out with 1 μl of nuclear extract (e.g., HA-TP2 extract, which is heparin-agarose enriched extract from activated Jurkat cells, or HA-R, which is heparin-agarose enriched extract from unactivated Jurkat cells) containing approximately 1.4 μg protein, 1–2 ng of $^{32}$P-labeled oligonucleotide duplexes containing the sequence 5'-CGAGGTCGACGGTATCGN NNNNNNNNNGGATCCACTAGTTCTAGAGC-3' (SEQ. ID No. 2), and 1 μg poly dI-dC in 10 μl of 10 mM HEPES pH 7.9, 0.5 mM DTT, 5 mM $MgCl_2$, 66 mM KCl, 50 μg/ml of tRNA. The oligonucleotides are labeled either by DNA polymerase I (Klenow fragment) in a exonuclease reaction followed by synthesis in the presence of a labeled nucleotide (s) or end-labeled with T4 polynucleotide kinase in the presence of $\gamma^{32}$P-ATP. The reaction mix is incubated for 10 min on ice. When oligonucleotide duplexes are added as competitors, they are added at a large excess (e.g., 50–1000 ng).

Protein-DNA complexes are separated from unbound oligonucleotide duplexes by electrophoresis on a 5% acrylamide-bisacrylamide (19:1) gel in 0.5×TBE buffer (1×TBE=90 mM Tris pH 8.3, 64.6 mM boric acid, 2.5 mM EDTA). The gel is dried onto Whatman 3MM paper or equivalent and autoradiographed. The area corresponding to bound duplexes is excised together with the 3MM paper and incubated at room temperature for 2 hrs. in distilled water After incubation, the tube is heated to 95° C. for 10–15 min, and briefly centrifuged. The clarified supernatant is precipitated with ethanol using glycogen as a carrier.

Approximately 50% of the recovered oligonucleotide duplexes is used in an amplification reaction. Amplification primers used are P1 (5'-CGAGGTCGACGGTATCG-3' (SEQ. ID No.3)), and P2, (5'-GCTCTAGAACTAGTGGATC-3' (SEQ. ID No.4)). In this experiment, four rounds of complex formation, electrophoretic separation, and amplification are performed. The final selected oligonucleotide duplexes are called TP2-4.

Example 3

CHARACTERIZATION OF BINDING SITES

The TP2-4 oligonucleotide duplexes are cloned in the pBluescript vector to obtain a library of binding sites, called TP2-4/BS. Twenty colonies are randomly picked and grown for plasmid isolation. The inserts of these 20 clones are evaluated by DNA sequence analysis. The DNA sequence is presented in the table below. The sequences are searched against the Transfac database (http://transfac.gbfbraunschweig.de/welcome.html). When a similarity of the sequence with previously known transcription factor binding site occurs, the associated factor is indicated. If the binding site is not found in the database, the factor is designated as "unknown".

TABLE 1

| NAME | BINDING SITE | FACTOR | EMSA | SEQ ID No. |
|---|---|---|---|---|
| BSN4 | ggaCCAATcg | CCAAT-bf[1] | nd | 7 |
| BSN7 | TGGGtGGGGT | SP1[2] | nd | 8 |
| BSN8 | accTGATAtg | GATA-1[3] | nd | 9 |
| BSN12 | gTGACTCccg | TPA Resp Ele[4] | nd | 10 |
| BSN20 | gcCAAGGTCg | ELP[5] | nd | 11 |
| BSN15 | CTTA CTcg | ANF[6] | Y | |
| BSN5-1 | cCcATCCATg | Pit-1[7] | N | 12 |
| BSN17 | GTAgCCATgt | Pit-1[7] | Y | 13 |
| BSN3 | ATGGTAGCGT | Unknown | N | 14 |
| BSN5-2 | TCGCAATGGG | Unknown | Y | 15 |
| BSN11 | GGTAATAGGN | Unknown | Y | 16 |
| BSN18-3 | CTGGATTATG | Unknown | N | 17 |
| BSN1 | GTGGGGGGTT | Unknown | nd | 18 |
| BSN6 | GTGGGAGGGT | Unknown | nd | 19 |
| BSN9 | CATGGCGGAC | Unknown | nd | 20 |
| BSN13 | GTCTAGGGAG | Unknown | nd | 21 |
| BSN14 | GGGGGGCTAT | Unknown | nd | 22 |
| BSN18-1 | GGGTTATAG | Unknown | nd | |
| 3BSN18-2 | GATTTGGACT | Unknown | nd | 23 | nd, indicates that the sequence was not analyzed by EMSA;
Y, indicates that the sequence exhibited specific shift by EMSA
N, indicates that the sequence did not exhibit a specific shift by EMSA
[1]see Mol. Cell Biol. 7:1530 (1987);
[2]see Nature 316:774 (1985);
[3]see Proc. Natl. Acad. Sci. USA 85:5976.(1988);
[4]see Cell 49:741 (1987);
[5]see Mol. Cell Biol. 9:4670 (1989);
[6]see Mol. Cell Biol. 10:3896 (1990); and
[7]see Genes Dev. 4:43 (1990)

Figure 2:
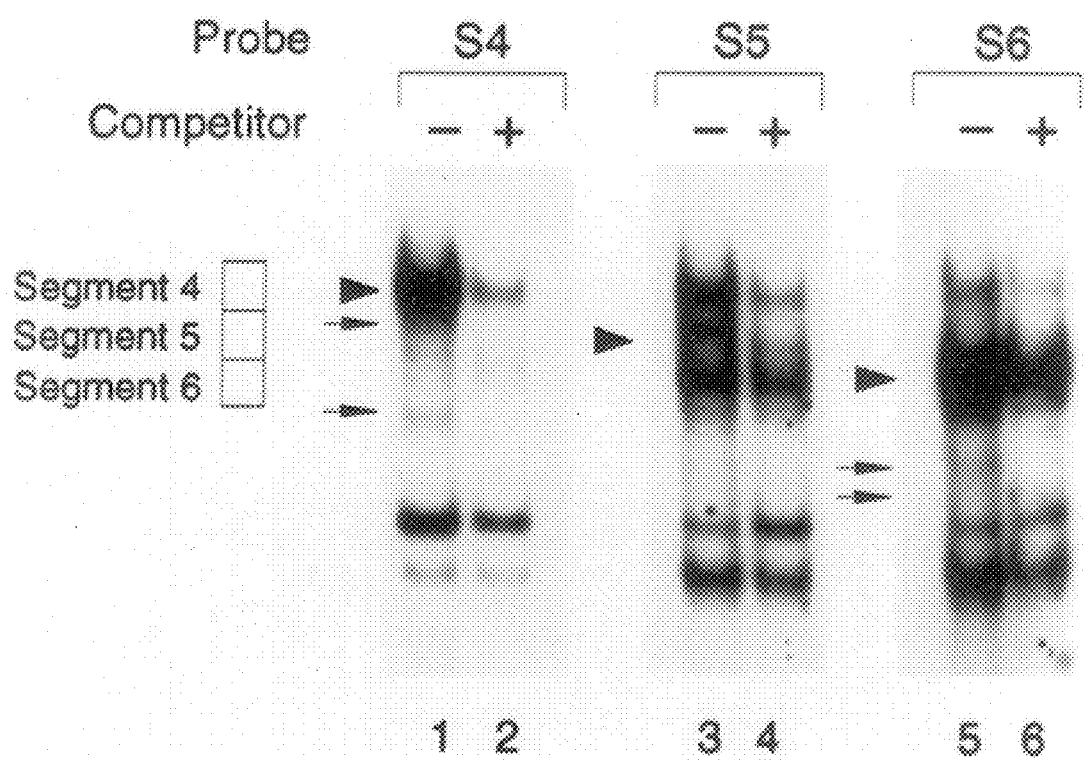
FIG. 2 is an autoradiogram of a gel shift assay showing reproducibility of band patterns. Complexes formed between TP2-4 oligonucleotide duplexes and HA-TP2 extract are electrophoresed. Duplexes present in a 1 cm length of the lane are isolated and used for subsequent complex formation. Complexes formed using oligonucleotide duplexes from segments 4, 5, and 6 (lanes S4, S5, and S6, respectively) that are within the corresponding segment region are marked by arrowheads. Additional complexes are marked by arrows.

Among these 20 clones, eight binding site sequences resemble recognition sites for known transcription factors. In particular, two sequences resemble binding sites for Pit-1, a POU-homeodomain transcription factor that is preferentially expressed in the pituitary gland (Lew and Elsholtz, *Nucleic Acids Res.* 19:6329, 1991) and expressed in lymphoid and other hematopoietic cells (Delhase et al., *Eur. J. Immunol.* 23:951, 1993). A third sequence resembles the binding site for ANF, a factor that negatively regulates the albumin enhancer in hepatocytes (Herbst et al., *Mol. Cell. Biol.* 10:3896, 1990), whose presence in T cells has not been previously demonstrated. In view of this, oligonucleotide duplexes containing sequences of these three known sites and four other unknown sites are synthesized and complexed with nuclear extract HA-TP2. The complexes are electrophoresed and analyzed by electrophoretic mobility shift analysis (EMSA). Of these, 4 exhibit specific shifts (FIG. 2). BSN17, one of the Pit-1-like sites, forms two distinctly migrating complexes with DNA-binding proteins in Jurkat cells, but only a single migrating complex in JY cells, thereby revealing Pit-1-like binding activities in lymphoid cells. The ANF-like site forms a single migrating complex. Furthermore, two of the four previously unknown sites show specific gel shifts. Assuming these sequences are representative, by extrapolation, at least two-thirds of the binding sites contained in the library represent authentic binding sites for DNA-binding proteins.

Although an accurate estimation of the total complexity of binding sites in the library is not possible, the low level of even imperfect repeats of binding site sequences in randomly sequenced clones suggests that thousands of sites are most likely represented. In addition, when multiple clones with the same binding site, such as the Ets-like binding sites are analyzed by DNA sequence analysis, the structures of individual clones are different, indicating that clones are not selectively amplified from an extremely small pool by a "Monte Carlo" effect. Such non-random amplifications are sometimes observed in amplification reactions using very small amounts of total template.

Figure 3:
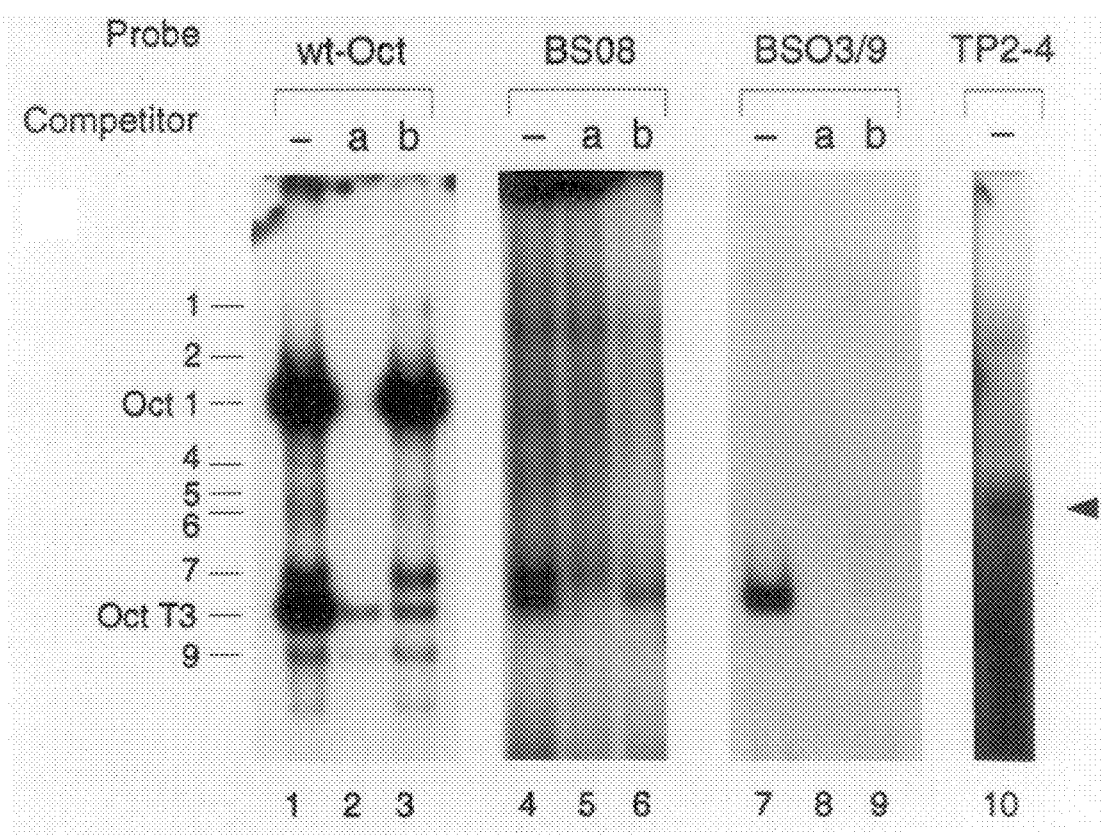
FIG. 3 is an autoradiogram of a gel-shift analysis of wt-Oct, BSO8, or BSO3/9 oligonucleotide duplexes complexed with HA-TP2 extract (lanes 1–9). Competitor oligonucleotide duplexes are: a, wt-Oct; b, BSO8. A single band observed in a gel-shift assay using bacterially-produced Oct2 protein and TP2-4 oligonucleotide duplexes is marked by an arrowhead (lane 10).

To verify reproducibility of the technique, oligonucleotide duplexes from a particular region of the gel are extracted and subjected to subsequent complex formation and electrophoretic analysis. An HA-TP2 nuclear extract is complexed with TP2-4 oligonucleotide duplexes extracted from various regions of a gel (segment 4, 5, and 6 indicated in FIG. 3). The segments are derived by dividing the upper third of a single lane of a gel into six 1 cm segments. In separate reactions, unlabeled oligonucleotide duplexes from the same region are added as competitor (lanes marked with a "+"). The reactions are then electrophoresed. As shown in FIG. 3, duplexes isolated from a particular region migrated to the same region in the subsequent reaction. Moreover, each of these DNA-protein complexes is competed to some extent by the oligonucleotide duplexes isolated from the corresponding region. Most of the segment probes showed additional competing bands revealing the presence of other proteins or protein complexes which would bind to the site(s) contained in that gel segment.

In addition, oligonucleotide duplexes from a region, segment 6, of the gel are cloned. DNA sequence analyses of inserts from 30 clones are presented in Table 2. In this table, core binding site sequences are indicated in bold typeface and sequences derived from the 5' and 3' flanking regions are indicated in lowercase letters. The sequences fall into three different consensus patterns: 13 conformed to the consensus pattern, RTGGGBGGRY, (S6-1) (SEQ ID No. 38); 8 to the consensus pattern YT/GRTAAA/CC/G (i.e., YKRTAAMS) (S6-2), and 5 to the consensus pattern A/TCCGGAAGY (i.e., WCCGGAAGY) (S6-3).

TABLE 2

| CLONE | SEQUENCE | SEQ ID No. |
|---|---|---|
| 6-2-2 | GGGGATGGGCggatcc | 25 |
| 6-3-1 | TAGTGTGGGTggatCC | 26 |
| 6-3-3 | ATTTATGGGGggatCC | 27 |

TABLE 2-continued

| CLONE | SEQUENCE | SEQ ID No. |
| --- | --- | --- |
| 6-5-1 | GTAGGTGGGCggatcc | 28 |
| 6-5-3R | CGGAAGTGGCCGatacc | 29 |
| 6-6-1 | GACACGTGATggatCC | 30 |
| 6-6-3 | TATGGGGGAA | 31 |
| 6-7-1 | GTGGGTGGGC | 32 |
| 6-9-1 | GATTATGGGTggatCC | 33 |
| 6-9-3 | GGTTGGGGGC | 34 |
| 6-11-2R | GTGGGCGGGG | 35 |
| 6-12-2R | GTGGGGGCTC | 36 |
| 6-12-3 | TGTCGTGGGTggatcc | 37 |
| consensus (1) | RTGGGBGGRY | 38 |
| 6-1 | AATTGTAAGC | 39 |
| 6-2-1 | TTAGGTAAAT | 40 |
| 6-5-2 | CGCTGTAATA | 41 |
| 6-6-2R | CCG TAAAGGG | 42 |
| 6-7-5R | GCCTATAACG | 43 |
| 6-9-2 | GGGATAAACGC | 44 |
| 6-10-1R | CATCTAACC | |
| 6-10-2 | CATCATAACC | 45 |
| consensus (2) | YKRTAAMS | |
| 6-3-2R | AACCGGAAGT | 46 |
| 6-4-IR | CGTACCGGAAGg | 47 |
| 6-8 | TCCGGAAGC | |
| 6-11-1 | TCCGGAAGC | |
| 6-11-3 | ACCGGAAGT | |
| consensus (3) | WCCGGAAGY | |

Figure 6:
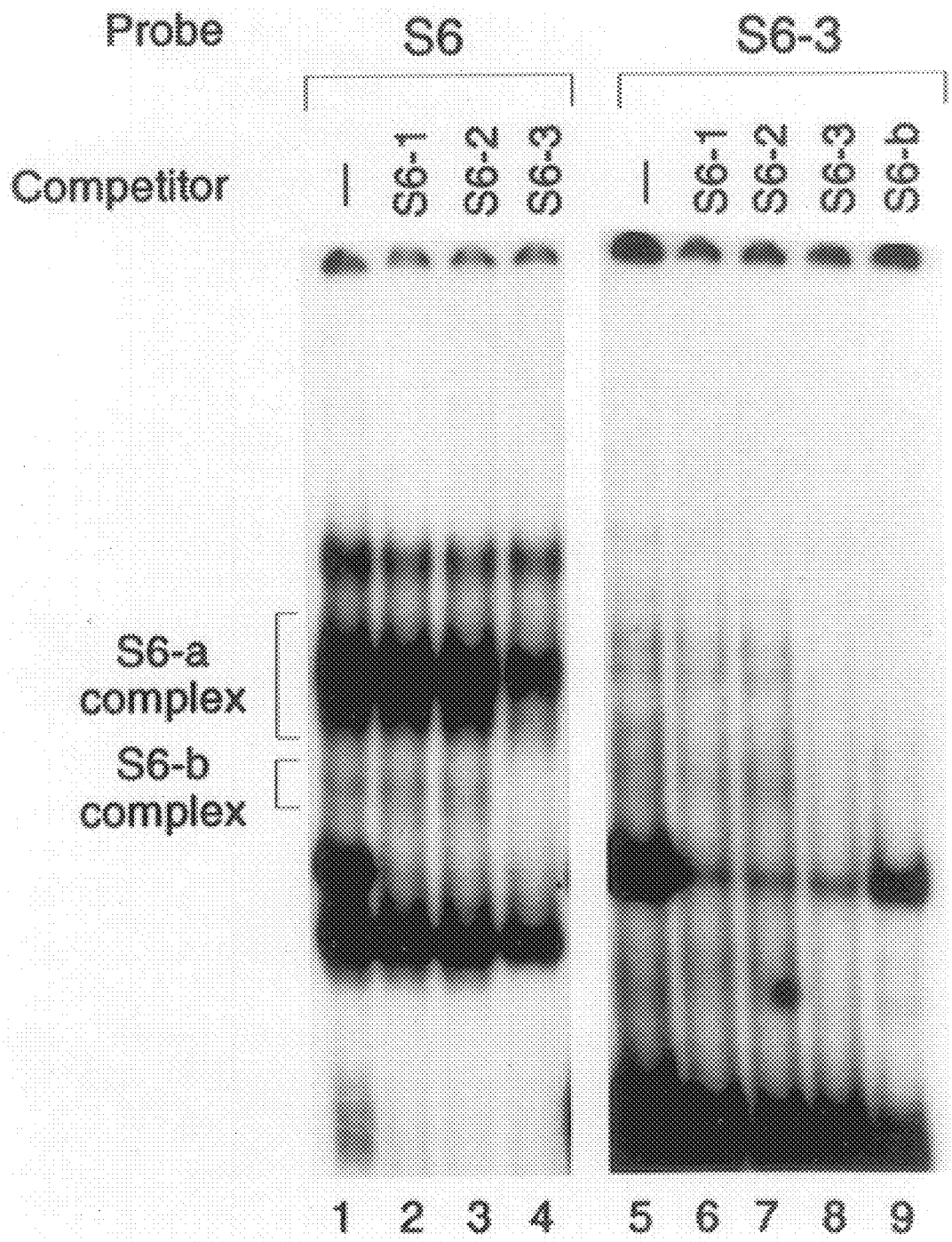
FIG. 6 is an autoradiogram of a gel-shift assay of S6 (lanes 1–4) or S6-3 (lanes 5–9) oligonucleotide duplexes complexed with HA-TP2 extract. Competitor oligonucleotide duplexes are S6-1 (lanes 2 and 6), S6-2 (lanes 3 and 7), S6-3 (lanes 4 and 8), and S6b (lane 9).

Oligonucleotide duplexes containing the consensus core sites are used for complex formation and called S6-1, S6-2, and S6-3. The S6-3 oligonucleotide duplex, but not the S6-1 or S6-2 oligonucleotide duplexes, compete with the duplexes extracted from S6b (FIG. 6, lane 4). Conversely, the complexes formed with the S6-3 duplex are competed equally well by S6-3 and S6-b oligonucleotide duplexes (FIG. 6, lanes 8 and 9 respectively), but not by other duplexes. This shows that the S6b bands are due to the S6-3 consensus sequence. The S6-3 consensus sequence has striking homology to binding sites for the Ets family of transcription factors (*Nucleic Acids Res.* 20:3, 1992; *J Exp. Med.* 175:1391, 1992).

A large family of Ets-like transcription factors have been identified. These include Ets-1 and Ets-2, which are expressed at high levels in T cells, the Tenary Complex Factors, Elk-1, Sap-1a, Sap-2, and Elf-1, a T cell-specific Ets protein. One component of the S6a band is a constitutively expressed factor, whose relative mobility on the gels is consistent with the molecular size of Elf-1. The S6b bands, however, may represent yet unidentified members of the Ets family. These complexes are not super-shifted by antisera to either Ets-1, Elf-1, GABP-α, or GABPβ, suggesting that additional, previously unknown, members of the Ets family of transcription factors are identified in T cells.

Example 4

ISOLATION AND CHARACTERIZATION OF DNA BINDING PROTEINS

Several factors in T cells are identified as binding to the wt-Octamer (wt-Oct) sequence (ATGCAAAT; *Proc. Natl. Acad. Sci. USA* 90:10260, 1993; *Mol. Cell Biol.* 13:5593, 1993; and *Mol. Cell Biol.* 13:5450, 1993). Octamer binding sites are present in TP2-4 oligonucleotide duplexes as evidenced by a band shift occurring when these duplexes are complexed with bacterially-produced Oct2 protein (FIG. 3, lane 10). However, when an oligonucleotide duplex comprising a wt-Oct sequence is complexed with an HA-TP2 extract, several bands are revealed. Moreover, these are specifically competed with wt-Oct (lanes a) oligonucleotide duplex (FIG. 3, lanes 1, 2). In particular, a prominent band reveals a binding protein, called OctT3, that is antigenically distinct from Oct1 and Oct2 (*Proc. Natl. Acad. Sci USA* 90:10260, 1993; *Science* 254:558, 1991). Prior attempts to clone a cDNA encoding OctT3 by screening bacterial expression libraries with a multimerized wt-Oct sequence were unsuccessful, although other cDNAs encoding proteins that specifically bind to the wt-Oct site were isolated.

Assuming that OctT3 binds a wt-Oct site at low affinity or fortuitously, other sequence sites, which are preferred for binding by OctT3, may be identified in the mixture of binding sites selected as described above. Thus, high affinity binding sites for OctT3 can be isolated from TP2-4 duplexes by competition of the OctT3-wt-Oct binding site complex. The TP2-4 oligonucleotide duplexes compete OctT3-wt-Oct complex, as well as bands 4 and 6-wt-Oct binding site complex. The OctT3 region of the gel is excised and the oligonucleotide duplexes in the complex are cloned. Inserts from eight random clones are subjected to DNA sequence analysis. Five clones contain an A-T rich sequence: 5'-AATAGAA-3', while three others contain G-C rich sequences that have the consensus pattern: 5'-TAGGDGBAGGG-3'(SEQ ID No. 24). The A-T rich sequence is used as part of oligonucleotide BSO8, 5'-GAATAGAACTGGATC-3' (SEQ ID No. 5); the G-C rich sequence is used as part of oligonucleotide BSO3/9, 5'-ATCGGTAGGKGSGTCGA-3' (SEQ ID No. 6).

When the BSO8 sequence is used as competitor, it strongly competes the OctT3-wt-Oct binding site complex and bands 4 and 6-wt-Oct binding site sequence, but not others (FIG. 3, lane 3). When an oligonucleotide duplex containing the BSO8 sequence is complexed with HA-TP2 extract, several bands of complexes are observed (FIG. 3, lane 4), which are competed by excess BSO8 sequence (FIG. 3, lane 6) but only partially competed by excess wt-Oct sequence (FIG. 3, lane 5). When BSO3/9 sequence is complexed with HA-TP2 extract, a single prominent band at a similar position to a major band seen when BSO8 sequence is used (FIG. 3, compare lanes 4 and 7). Furthermore, binding to BSO3/9 sequence is competed by BSO8 sequence as well as wt-Oct (FIG. 3, lanes 8 and 9, respectively), suggesting that factors that bind to the BSO3/9 sequence are a subset of those that bind to the BSO8 probe. Taken together, these results strongly suggest that BSO8 sequence is an optimal binding site for the OctT3 protein and may be used to screen an appropriate library for OctT3.

Figure 4A:
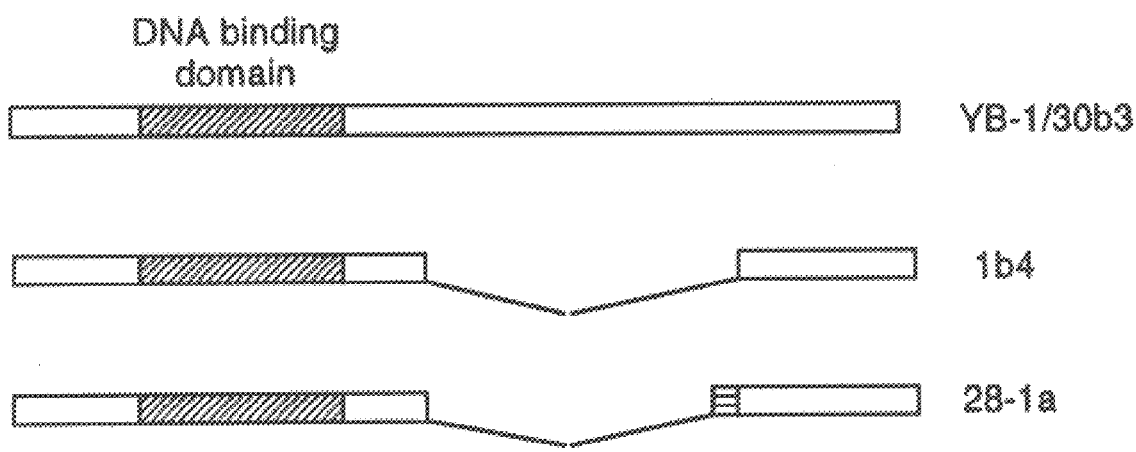
FIGS. 4A and 4B depict the structure and binding specificities of three Oct-T3 cDNAs. Panel A is a schematic drawing showing the relationship of three cDNA clones. Panel B shows the results of lacZ-Oct-T3 fusion polypeptides complexed with either BSO8 or wt-Oct oligonucleotide duplexes.

An expression cDNA library in λgt 11 is constructed from Jurkat T cell mRNA and screened with labeled BSO8 oligonucleotide duplex. From this screening, four cDNAs are isolated, all of which are members of a family of transcription factors termed the Y-box binding proteins. One of the clones, 30b3 is identical to YB-1 (*Proc. Natl. Acad. Sci. USA* 85:7322, 1988). Two other clones are presumptive splice variants of YB-1 cDNA (FIG. 4a). Clone 1b4 lacks 96 internal amino acids (residues 158 through to 245), while clone 28-1a lacks 108 amino acids (from residue 158 through to 256). Clone 5b4 is identical to the dbpA gene (GenBank Accession No. M24069), a member of the "cold shock" family of transcription factors. Thus, OctT3 is a member of the Y-box family of transcription factors.

A comparison of part of the BSO8 and BSO3/9 consensus sequences with the HLA class II DRA promoter sequence is shown below. In this promoter, the Y-box sequence (AATCAG); the X-box sequence (CTAG); and the consensus wt-Oct sequence (ATGCAAAT) are underlined. The number of intervening nucleotides between these boxes are shown in parentheses.

```
                                                          SEQ ID Nos.
BSO8                      AAT_AGAA
DRA Promoter  ATGCAAAT(N₁₆)  AATCAGAA(N₂₆)  CTAGGGGAAGGG       1
BSO3/9                                      CTAG
```

Figure 4B:
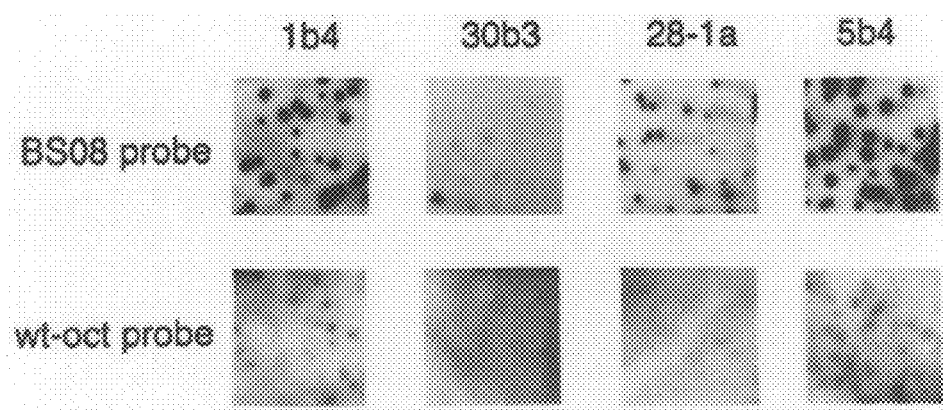

The OctT3lacZ fusion protein from λgt11 is isolated and used in complex formation with BSO8 and wt-Oct oligo-nucleotide duplexes. A comparison of the relative intensities with which the lacZ-fusion protein binds the BSO8 and wt-Oct duplexes (FIG. 4B) confirms that BSO8 sequence is a preferred binding site over wt-Oct sequence.

The reason(s) that multiple complexes form with the BSO8 probe and only a single complex forms with the BSO3/9 probe are presently unclear. However, recently, YB-1 has been shown to bind to regions of both the X-box and the Y-box (MacDonald et al., *J Biol. Chem.* 270:3527, 1995). Furthermore, a consensus octamer site is present adjacent to the Y-box motif in the DRA promoter, and may account for the multiple complexes.

Example 5

MULTIPLE SELECTION TECHNIQUE USING ACTIVATED AND UNACTIVATED CELLS

Figure 5:
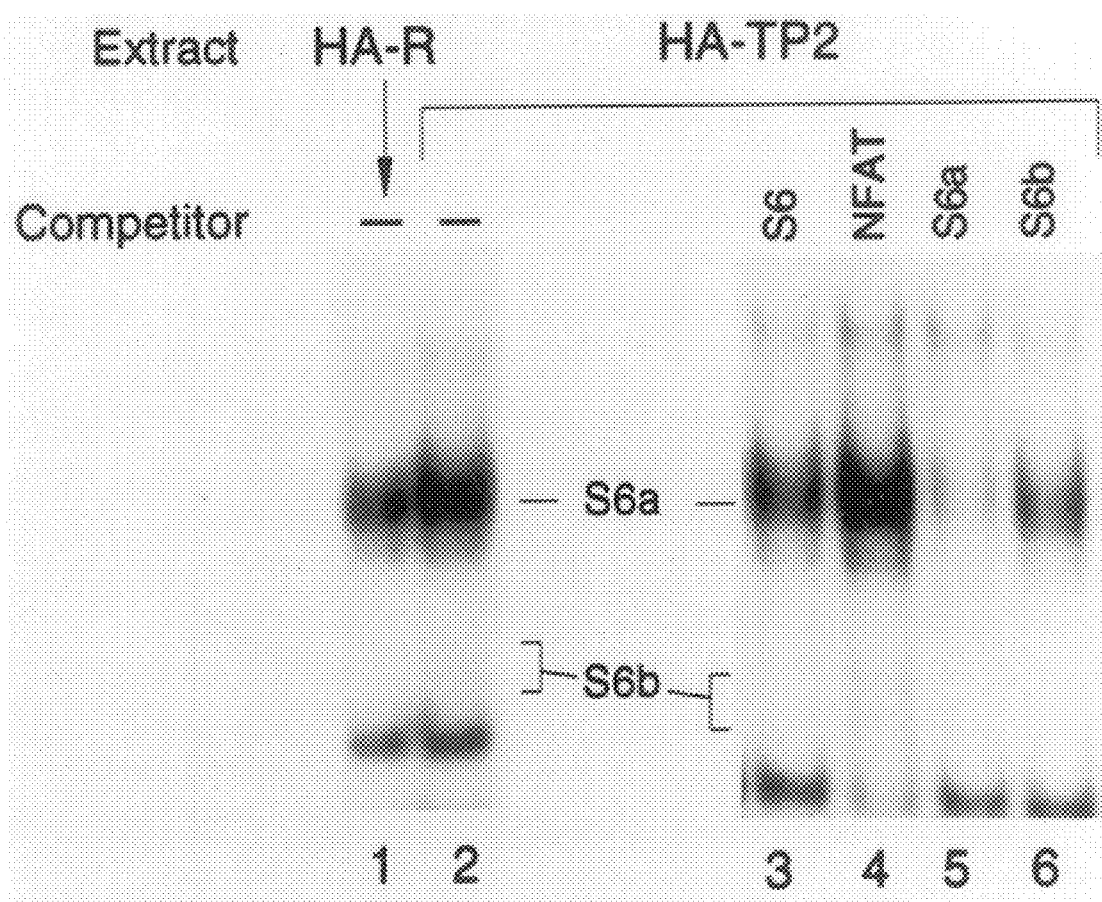
FIG. 5 is an autoradiogram of a gel-shift analysis of S6 oligonucleotide duplexes with either HA-R (lane 1) or HA-TP2 (lanes 2–6) extracts. Competitor oligonucleotide duplexes are S6 (lane 3), NF-AT (lane 4), S6a (lane 5), and S6b (lane 6).

A subset of oligonucleotide duplexes is employed to compare differences in factor binding activities between quiescent and activated Jurkat cells. Oligonucleotide duplexes from segment 6 (S6) are used in complex formation with the HA-TP2 (activated Jurkat cells) or HA-R (quiescent or unactivated Jurkat cells) extract. As shown in FIG. 5, two additional bands, called S6b, are present in activated Jurkat cells (lane 2) but absent in quiescent Jurkat cells (lane 1). These bands are competed by excess of S6 oligonucleotide duplexes (lane 3), and also by the extracted S6a oligonucleotide duplex(es) (lane 5). The S6b oligonucleotide duplexes, however, only partially competed the S6a complex (lane 6), suggesting that S6a band might contain more than one comigrating DNA-protein complex.

The transcription factor, N-FAT, is known to be activated early during T cell activation. However, the N-FAT binding site (*Nature* 352:803, 1991) does not compete any of the specific bands resulting from complex formation with the S6 oligonucleotide duplexes (lane 4); although it forms complexes that are competed by excess unlabeled N-FAT binding site. This indicates that the DNA-binding protein(s) in the S6b bands extracts is distinct from N-FAT.

Example 6

MULTIMERIZATION OF PROTEIN-BINDING SITES FOR ANALYSIS

To facilitate analysis of selected binding sites, the selected binding sites are excised from the oligonucleotide duplexes and multimerized.

An oligonucleotide duplex is designed with EcoRI sites (double underlined) flanking the potential binding site. The DNA sequence of the oligonucleotide, P4-R, is presented as SEQ ID No: 48 and as below:

5'-CGATGGTAGAGGTGTGTGC<u><u>TGAATTC</u></u>AGNNNNNNNNNNCG<u><u>GAATTC</u></u>ACGTCGATCTTAGAACTGA-3'

As described above, the oligonucleotide duplex is incubated with a nuclear extract and complexes are isolated after gel electrophoresis. The duplexes present in the complexes are amplified with primers that contain a biotin group at the 5' end. The DNA sequences for the forward and reverse amplification primers, P4-1 and P4-2, are presented as SEQ ID Nos.: 49 and 50 and as below:

5'-CGATGGTAGAGGTGTGTGC-3'  (P4-1)

5'-TCAGTTCTAAGATCGACGT-3'  (P4-2)

Amplification conditions use a 1:10 dilution of Opti-prime buffer #2 (Stratagene Cloning Systems (SCS), La Jolla, Calif.), 1:50 dilution of 50×Master Mix Buffer (SCS) and 1.25 U/reaction of Taq DNA polymerase. Cycle conditions are: 95° C., 5 min, followed by 35 cycles of 95° C., 30 sec; 65° C., 15 sec; 72° C. sec, followed by hold at 4° C.

The amplified material is extracted with phenol:chloroform (1:1 v/v) and precipitated with ethanol. The DNA is resuspended in 10 mM TRIS, 1 mM EDTA and chromatographed on a Centri-Spin-20 column (Princeton Separation, Adelphia, N.J.). The eluant is digested with EcoRI. At the end of the digestion reaction, the enzyme is heat-inactivated. The reaction is then passed over streptavidin-coupled beads (Dynal, Norway) to remove the non-binding site portions of the oligonucleotide duplex. The flow-through material is desalted on a SEPHADEX G-50 spin column (Quick-Spin; Boehringer-Mannheim, Indianapolis, Ind.). DNA in the eluant is precipitated with ethanol. The DNA is resuspended in water. The EcoRI-digested material is ligated for several hours at 14° C. in 1× ligase buffer and TG DNA ligase after which the multimerized mixture is ligated into the EcoRI site of PCR-script vector DNA. After ligation, the material is introduced into bacteria. Following transformation and growth on selection plates, 96 different colonies are picked and the inserts sized by amplification using the M13 forward and M13 reverse sequencing primers. The average insert size is 2–3 binding sites and one clone had 25 binding sites.

It will be appreciated that, although specific embodiments of the invention have been described herein for purposes of illustration, various modifications may be made without departing from the spirit and scope of the invention. Accordingly, the invention is not limited except as by the appended claims.

We claim:

1. A method for isolating DNA-binding proteins, comprising:

(a) mixing (i) a set of oligonucleotide duplexes, wherein said duplexes comprise 5' and 3' sequences that will hybridize to primers for amplification and a randomly generated internal sequence of nucleotides, (ii) an inhibitor of non-sequence specific binding of DNA-binding proteins to the oligonucleotide duplexes and (iii) a sample containing a mixture of DNA-binding proteins under conditions in which the concentration of oligonucleotide duplexes is at or below the average Kd value for specific binding between the oligonucleotide duplexes and the DNA-binding proteins;

(b) separating unbound oligonucleotide duplexes from oligonucleotide duplexes complexed with the DNA-binding proteins on the basis of differences in physical or biochemical properties;

(c) recovering the DNA-binding proteins from the complexes.

2. The method of claim 1, further comprising, subsequent to step (b):

amplifying complexed duplexes to form amplified duplexes;

mixing the amplified duplexes with the sample containing DNA-binding proteins; and separating unbound amplified duplexes from amplified duplexes complexed with the DNA-binding proteins on the basis of differences in physical or biochemical properties;

wherein the amplifying, mixing, and separating steps are performed one or more times.

3. The method of claim 2 wherein the steps are performed three times.

4. The method of claim 1, wherein the sample is a nuclear extract or a cellular extract.

5. The method of claim 1 wherein the internal sequence contains 6 to 25 base pairs.

6. The method of claim 1 wherein the internal sequence contains 8 to 12 base pairs.

7. The method of claim 1 wherein the non-specific inhibitor is poly(dI-dC).

8. The method of claim 1 wherein the 5' and 3' sequences contain 10 to 30 bp.

9. The method of claim 1 wherein the 5' and 3' sequences are different.

10. The method of claim 1 wherein the separating step is based on differences in electrophoretic or chromatographic mobility.

11. The method of claim 10 wherein the separating step uses polyacrylamide gel electrophoresis or size-exclusion chromatography.

12. The method of claim 1 wherein the separating step is based on differences in filter-binding properties.

13. A method for identifying DNA-binding proteins in an expression library, comprising:

(a) mixing (i) a set of oligonucleotide probes wherein said probes comprise 5' and 3' sequences that will hybridize to primers for amplification and a randomly generated internal sequence of nucleotides, (ii) an inhibitor of non-sequence specific binding of DNA-binding proteins to the oligonucleotide probes and (iii) a mixture of DNA binding proteins from an expression library, wherein said library comprises cells that express DNA-binding proteins, under conditions in which the concentration of oligonucleotide probes is at or below the average Kd value for specific binding between the oligonucleotide probes and the DNA-binding proteins;

(b) separating on the basis of differences in physical or biochemical properties unbound oligonucleotide probes from oligonucleotide probes complexed with the DNA-binding proteins;

(c) amplifying complexed probes to form amplified probes; and (d) detecting the binding of amplified probes to the DNA binding proteins of the expression library;

whereby cells in the expression library that express DNA-binding proteins are identified.

14. The method of claim 13, further comprising the step of isolating cells in the expression library expressing DNA binding proteins that bind said amplified probes.

15. A method for simultaneously determining nucleotide recognition sequences for a mixture of DNA-binding proteins, comprising:

(a) mixing (i) a set of oligonucleotide duplexes wherein said probes comprise 5' and 3' sequences that will hybridize to primers for amplification and a randomly generated internal sequence of nucleotides, (ii) an inhibitor of non-sequence specific binding of DNA-binding proteins to the oligonucleotide duplexes and (iii) a sample containing a mixture of DNA-binding proteins under conditions in which the concentration of oligonucleotide duplexes is at or below the average Kd value for specific binding between the oligonucleotide duplexes and the DNA-binding proteins;

(b) separating unbound oligonucleotide duplexes from oligonucleotide duplexes complexed with the DNA-binding proteins on the basis of differences in physical or biochemical properties;

(c) amplifying complexed duplexes to form amplified duplexes; and (d) analyzing the amplified duplexes to determine nucleotide recognition sequences for the DNA-binding proteins.

16. The method of claim 15 wherein the analyzing step comprises:

ligating the amplified duplexes to a vector to generate clones; and determining the DNA sequences of the cloned duplexes.

17. The method of claim 15 wherein the analyzing step comprises:

denaturing the amplified duplexes;

hybridizing the denatured duplexes to an array of single-stranded oligonucleotides having sequences; and detecting oligonucleotides hybridized with denatured duplexes.

18. A method for simultaneously isolating nucleotide recognition sequences for a mixture of DNA-binding proteins, comprising:

(a) mixing a set of oligonucleotide duplexes wherein said probes comprise 5' and 3' sequences that will hybridize to primers for amplification and a randomly generated internal sequence of nucleotides, an inhibitor of non-sequence specific binding of DNA-binding proteins to the oligonucleotide duplexes and a sample containing a mixture of DNA-binding proteins under conditions in which the concentration of oligonucleotide duplexes is at or below the average Kd value for specific binding between the oligonucleotide duplexes and the DNA-binding proteins;

(b) separating unbound oligonucleotide duplexes from oligonucleotide duplexes complexed with the DNA-binding proteins on the basis of differences in physical or biochemical properties weight;

(c) amplifying complexed duplexes to form amplified duplexes;

thereby isolating nucleotide recognition sequences for DNA-binding proteins.

19. The method of claim 18, further comprising, subsequent to step (c):

(c)(1) mixing the amplified duplexes with the sample containing DNA-binding proteins;

(c)(2) separating unbound amplified duplexes from amplified duplexes complexed with the DNA-binding proteins on the basis of differences in molecular weight; and (c)(3) amplifying the complexed duplexes from step (c)(2) to form amplified duplexes;

wherein steps (c)(1) through (c)(3) are performed one or more times.

20. The method of claim 19 wherein steps (c)(1) to (c)(3) are performed three times.

21. The method of claim 18 wherein the 5' and 3' sequences each have a restriction site.

22. The method of claim 21 wherein the restriction sites are identical.

23. The method of claim 18 wherein the sample is a nuclear extract, cellular extract, or an extract from cells of an expression library.

24. The method of claim 18 wherein the internal sequence contains 6 to 25 base pairs.

25. The method of claim 18 wherein the non-specific inhibitor is poly(dI-dC).

26. The method of claim 18 wherein the separating step uses polyacrylamide gel electrophoresis.

27. The method of claim 18 wherein the oligonucleotide duplexes are labeled.

28. The method of claim 18 wherein the oligonucleotide duplexes comprise a tag moiety.

29. The method of claim 28 wherein said tag moiety is linked to the 5' and 3' ends of the duplexes.

30. The method of claim 29 wherein the tag moiety is biotin or a fluorescent dye.

* * * * *